(12) United States Patent
Fink et al.

(10) Patent No.: US 7,131,945 B2
(45) Date of Patent: Nov. 7, 2006

(54) OPTICALLY POWERED AND OPTICALLY DATA-TRANSMITTING WIRELESS INTRAOCULAR PRESSURE SENSOR DEVICE

(75) Inventors: Wolfgang Fink, Montrose, CA (US); Eui-Hyeok Yang, Stevenson Ranch, CA (US); Yoshi Hishinuma, Arcadia, CA (US); Choonsup Lee, Pasadena, CA (US); Thomas George, La Canada, CA (US); Yu-Chong Tai, Pasadena, CA (US); Ellis Meng, Pasadena, CA (US); Mark Humayun, Glendale, CA (US)

(73) Assignees: California Institute of Technology, Pasadena, CA (US); Doheny Eye Institute, Los Angeles, CA (US)

( * ) Notice: Subject to any disclaimer, the term of this patent is extended or adjusted under 35 U.S.C. 154(b) by 389 days.

(21) Appl. No.: 10/686,492

(22) Filed: Oct. 14, 2003

(65) Prior Publication Data

US 2004/0116794 A1    Jun. 17, 2004

Related U.S. Application Data

(60) Provisional application No. 60/419,014, filed on Oct. 16, 2002, provisional application No. 60/446,403, filed on Feb. 11, 2003.

(51) Int. Cl.
    *A61B 3/16*    (2006.01)

(52) U.S. Cl. .................................................. 600/398
(58) Field of Classification Search ................ 600/398, 600/399, 400, 401, 402, 403, 404, 405

See application file for complete search history.

(56) References Cited

U.S. PATENT DOCUMENTS

| | | | |
|---|---|---|---|
| 3,406,681 A * | 10/1968 | Zandman | 600/398 |
| 4,089,329 A * | 5/1978 | Couvillon et al. | 600/398 |
| 4,305,399 A * | 12/1981 | Beale | 600/398 |
| 4,476,876 A * | 10/1984 | Uchiyama | 600/495 |
| 4,523,597 A | 6/1985 | Sawa et al. | |
| 4,548,205 A | 10/1985 | Armeniades et al. | |
| 4,601,545 A * | 7/1986 | Kern | 349/200 |
| 4,722,350 A | 2/1988 | Armeniades et al. | |
| 4,817,620 A | 4/1989 | Katsuragi et al. | |
| 4,922,913 A | 5/1990 | Waters, Jr. et al. | |
| 4,947,849 A | 8/1990 | Takahashi et al. | |
| 4,951,670 A | 8/1990 | Tanaka et al. | |
| 4,951,671 A | 8/1990 | Coan | |
| 4,987,899 A | 1/1991 | Brown | |
| 5,002,056 A | 3/1991 | Takahashi et al. | |
| 5,005,577 A | 4/1991 | Frenkel | |
| 5,042,483 A | 8/1991 | Nishio | |
| 5,107,851 A | 4/1992 | Yano et al. | |
| 5,148,807 A | 9/1992 | Hsu | |
| 5,165,409 A | 11/1992 | Coan | |
| 5,176,139 A | 1/1993 | Fedorov et al. | |
| 5,179,953 A * | 1/1993 | Kursar | 600/399 |

(Continued)

*Primary Examiner*—Max F. Hindenburg
*Assistant Examiner*—Matthew D. Dryden
(74) *Attorney, Agent, or Firm*—Fish & Neave IP Group

(57) ABSTRACT

An implantable intraocular pressure sensor device for detecting excessive intraocular pressure above a predetermined threshold pressure is disclosed. The device includes a pressure switch that is sized and configured to be placed in an eye, wherein said pressure switch is activated when the intraocular pressure is higher than the predetermined threshold pressure. The device is optically powered and transmits data wirelessly using optical energy. In one embodiment, the pressure sensor device is a micro electromechanical system.

40 Claims, 8 Drawing Sheets

U.S. PATENT DOCUMENTS

| | | |
|---|---|---|
| 5,190,042 A | 3/1993 | Hock |
| 5,197,473 A | 3/1993 | Fedorov et al. |
| 5,217,015 A * | 6/1993 | Kaye et al. ................. 600/405 |
| 5,279,300 A | 1/1994 | Miwa et al. |
| 5,299,573 A | 4/1994 | Kobayashi |
| 5,349,955 A | 9/1994 | Suzuki |
| 5,355,884 A | 10/1994 | Bennett |
| 5,375,595 A | 12/1994 | Sinha et al. |
| 5,396,888 A | 3/1995 | Massie et al. |
| 5,465,123 A | 11/1995 | Iijima |
| 5,476,484 A * | 12/1995 | Hedberg ..................... 607/23 |
| 5,523,808 A | 6/1996 | Kohayakawa |
| 5,546,941 A | 8/1996 | Zeimer et al. |
| 5,634,463 A | 6/1997 | Hayafuji |
| 5,636,635 A | 6/1997 | Massie et al. |
| 5,671,737 A | 9/1997 | Harosi |
| 5,727,551 A | 3/1998 | Takagi |
| 5,735,275 A | 4/1998 | Ballou et al. |
| 5,776,061 A | 7/1998 | Hayafuji |
| 5,810,005 A | 9/1998 | Dublin, Jr. et al. |
| 5,830,139 A | 11/1998 | Abreu |
| 5,833,606 A | 11/1998 | Haraguchi |
| 5,865,742 A | 2/1999 | Massie |
| 5,865,764 A | 2/1999 | Moorhead |
| 5,946,073 A | 8/1999 | Miwa |
| 5,947,898 A | 9/1999 | Suzuki et al. |
| 5,964,704 A | 10/1999 | Hayafuji |
| 5,989,195 A | 11/1999 | Iijima et al. |
| 6,016,102 A | 1/2000 | Fortune |
| 6,030,343 A | 2/2000 | Chechersky |
| 6,042,544 A | 3/2000 | Miwa et al. |
| 6,053,867 A | 4/2000 | Iijima |
| 6,093,147 A | 7/2000 | Kontiola |
| 6,110,110 A | 8/2000 | Dublin, Jr. et al. |
| 6,123,668 A | 9/2000 | Abreu |
| 6,168,575 B1 | 1/2001 | Soltanpour |
| 6,193,656 B1 | 2/2001 | Jeffries et al. |
| 6,234,966 B1 | 5/2001 | Miwa |
| 6,361,495 B1 | 3/2002 | Grolman |
| 6,394,968 B1 | 5/2002 | Wallace |
| 6,423,001 B1 * | 7/2002 | Abreu ....................... 600/405 |
| 6,440,070 B1 | 8/2002 | Israel |
| 6,443,893 B1 | 9/2002 | Schnakenberg |
| 6,447,449 B1 | 9/2002 | Fleischman |
| 6,517,483 B1 | 2/2003 | Park et al. |
| 6,524,243 B1 * | 2/2003 | Fresco ....................... 600/399 |
| 6,537,215 B1 | 3/2003 | Miwa |
| 6,547,734 B1 | 4/2003 | Madsen et al. |
| 6,579,235 B1 * | 6/2003 | Abita et al. ................. 600/398 |
| 6,595,920 B1 | 7/2003 | Walton |
| 6,602,192 B1 | 8/2003 | Miwa |
| 6,939,299 B1 * | 9/2005 | Petersen et al. ............ 600/398 |
| 2002/0128546 A1 | 9/2002 | Silver |
| 2002/0151816 A1 | 10/2002 | Rich et al. |
| 2002/0173711 A1 | 11/2002 | Walton |
| 2002/0193674 A1 | 12/2002 | Fleischman et al. |
| 2002/0193675 A1 | 12/2002 | Rathjen |
| 2003/0078487 A1 | 4/2003 | Jeffries et al. |

* cited by examiner

OPTICALLY POWERED AND OPTICALLY DATA-TRANSMITTING WIRELESS INTRAOCULAR PRESSURE SENSOR DEVICE

CROSS-REFERENCE TO RELATED APPLICATION

The present application claims the benefits of provisional application Ser. No. 60/419,014, filed Oct. 16, 2002, and provisional application Ser. No. 60/446,403, filed Feb. 11, 2003; the entire contents of which are incorporated herein by reference.

FIELD OF THE INVENTION

The present invention generally relates to an improved medical device and methods for sensing the elevated pressure in organs of the human body. More particularly, the present invention relates to an intraocular pressure sensor that is accurate and small enough to be implantable in the eye to continuously or on demand monitor the intraocular pressure in ocular hypertensives and patients with glaucoma, thus helping to prevent the onset of damage from glaucoma and to monitor effects of glaucoma therapy.

BACKGROUND OF THE INVENTION

Glaucoma is a disease affecting millions of people in the US alone every year. Elevated intraocular pressure (IOP), the most common cause of glaucoma, slowly kills the ganglion cell axons (which collectively form the optic nerve) affecting the peripheral visual field and progressing to the center. If untreated, glaucoma leads to blindness. In general, visual field loss caused by glaucoma is irreversible.

The usual treatment for glaucoma can be as simple as administering eye drops. Most of current therapies for glaucoma are directed toward decreasing intraocular pressure. Currently recognized categories of drug therapy for glaucoma include: (1) Miotics (e.g., pilocarpine, carbachol, and acetylcholinesterase inhibitors), (2) Sympathomimetics (e.g., epinephrine and dipivalylepinephxine), (3) Beta-blockers (e.g., betaxolol, levobunolol and timolol), (4) Carbonic anhydrase inhibitors (e.g., acetazolamide, methazolamide and ethoxzolamide), and (5) Prostaglandins (e.g., metabolite derivatives of arachindonic acid). Medical therapy includes topical ophthalmic drops or oral medications that reduce the production of aqueous from a ciliary body or increase the outflow of aqueous out of the trabecular meshwork of the eye.

The aqueous or aqueous humor is a transparent liquid that fills the region (anterior chamber) between the cornea at the front of the eye and the lens. The aqueous humor is constantly secreted by the ciliary body around the lens, so there is a continuous flow of the aqueous humor from the ciliary body to the eye's anterior chamber. The eye's pressure is determined by a balance between the production of aqueous and its exit through the trabecular meshwork and Schlemm's canal (major route) or via uveal scleral outflow (minor route).

There are a number of external eye pressure measuring devices. All devices indent the cornea to measure pressure and they do so directly by contacting it or indirectly by a non-contact method (i.e., pneumatic displacement "air puff"). For example, a Tono-pen manufactured by Medtronic Solan (Jacksonville, Fla.) utilizes micro strain gage technology with battery power and a 1.5 mm transducer tip to gently contact the cornea and display the average of four independent readings along with a statistical coefficient. Both contact and non-contact tonometers are very dependent on the eye wall and corneal rigidity and can be grossly wrong because these factors are not taken into account. In addition to the problems of imprecision with most of the external IOP measuring devices, at least the contact ones can only be administered in physicians' offices.

More realistic IOP measurements can be obtained from within the eye. For this purpose a variety of devices have been either proposed or developed recently. However, none of the micromachined devices are being used as a standard method to measure IOP because they are too invasive to be implanted and/or have not been validated in a realistic variable pressure environment (e.g., in an animal eye).

U.S. Pat. No. 6,579,235 issued on Jun. 17, 2003, the entire contents of which are incorporated herein by reference, discloses a device for passively measuring intraocular pressure of a patient including an in vivo sensor and an instrument external to the patient for remotely energizing the sensor, thereby permitting the instrument to determine the intraocular pressure. The device directly and continuously measures the intraocular pressure of a patient. The in vivo sensor in the intraocular pressure monitor includes a capacitive pressure sensor and an inductive component. An instrument, external to the patient, measures the pressure, provides readout of the pressure values and determines the intraocular pressure.

U.S. Pat. No. 6,602,192 issued on Aug. 5, 2003, the entire contents of which are incorporated herein by reference, discloses a non-contact type tonometer monitoring the rate of change in pressure between a standard curve and a measured curve and calculating an intraocular pressure of the patient's eye based on the amended pressure changing curvature.

U.S. Pat. No. 6,537,215 issued on Mar. 25, 2003, the entire contents of which are incorporated herein by reference, discloses a non-contact type tonometer including a compressed air blowing unit that blows the compressed air to a cornea of an examinee's eye; an optical system which projects light to the cornea; a photosensor which detects reflection light reflected from the cornea; and a controller which obtains a change in pressure for a predetermined time based on detection results by the pressure sensor when the photosensor detects a predetermined change amount of the reflection light.

U.S. Pat. No. 6,524,243 issued on Feb. 25, 2003, the entire contents of which are incorporated herein by reference, discloses an applanation tonometer for measuring pressure within a human eye comprising an electrical measurement apparatus which detects the mechanical displacement of a plunger, the displacement of the plunger reflecting an intraocular pressure, and the electrical measurement apparatus converting the corresponding mechanical displacement of the plunger into an electrical signal and display.

U.S. Pat. No. 6,447,449 issued on Sep. 10, 2002, the entire contents of which are incorporated herein by reference, discloses a tonometer sensor for disposition in proximity to a portion of a surface of the eye comprising a substrate including a contact surface for making contact with the surface portion of the eye. The contact surface includes an outer non-compliant region and an inner compliant region fabricated as an impedance element that varies in impedance as the inner region changes shape. A first region of material is responsive to a non-invasive external force to press the contact surface against the surface portion of the eye and cause the compliant region to change shape in proportion to an intraocular pressure of the eye. A second region of conductive material is electrically coupled to the impedance element of the compliant region and is responsive to an external signal for energizing the impedance element so that the intraocular pressure is determined.

U.S. Pat. No. 6,443,893 issued on Sep. 3, 2002, the entire contents of which are incorporated herein by reference, discloses a device for measuring intraocular pressure comprising: a remote measuring device adapted to be implanted in an eye, the remote measuring device having a pressure sensor, a converter for converting sensor signals into information for wireless transmission, and a transmitter; a receiver adapted to be located outside the eye for receiving information transmitted by the transmitter; and an evaluation device for converting information received into data expressing the intraocular pressure and for recording the data, wherein the remote measuring device further includes a data logger in which measurement data continuously supplied by the pressure sensor is stored and from which the measurement data is called up at certain times in operation of the converter.

None of the above-cited prior art discloses an optically powered and optically data-transmitting wireless intraocular pressure sensor, suitable for being implanted in the eye and for monitoring the IOP continuously or on demand. Moreover, none of the above-cited prior art discloses a solar cell system-powered or battery-powered wireless intraocular pressure sensor. Therefore, these aspects of the present invention provide a wireless intraocular pressure sensor (WIPS) that enables detecting IOP violating a predetermined pressure threshold.

SUMMARY OF THE INVENTION

It is one object of the present invention to provide an optically powered and optically data-transmitting wireless pressure sensor device for detecting excessive intraocular pressure above a predetermined threshold pressure, comprising a pressure switch that is sized and configured to be placed in the anterior chamber of an eye, wherein the pressure switch is activated when the intraocular pressure is higher than the predetermined threshold pressure. In one embodiment, the pressure switch is a resettable pressure switch.

It is another object of the invention to provide an optically powered and optically data-transmitting wireless intraocular pressure sensor device for detecting excessive intraocular pressure above a plurality of threshold pressures, comprising a plurality of pressure switches that are sized and configured to be placed in the anterior chamber of an eye, wherein a first pressure switch is activated when the intraocular pressure is higher than a first predetermined threshold pressure, and wherein a second pressure switch is activated when the intraocular pressure is higher than a second predetermined threshold pressure, and so forth.

In one embodiment, the pressure sensor device is a micro electromechanical system. In another embodiment, the pressure sensor device is placed on the iris of an eye or on an intraocular lens or on a glaucoma tube to enable the device for external data readout. In still another embodiment, the pressure sensor device is powered by a solar cell system or by a battery, the power source either implanted along with the device or wired externally to the device.

Some aspects of the invention relate to the pressure switch system comprising a first electrode and a second electrode mounted onto a compressible enclosure (filled with gas or vacuum), the electrodes being sized, configured and positioned spaced apart when the intraocular pressure is lower than the predetermined threshold pressure, and wherein the first electrode contacts the second electrode to make a closed electric circuit when the intraocular pressure becomes higher than the predetermined threshold pressure. One aspect of the invention provides a timer to record the time, date, and duration of activity. Another aspect of the invention provides a resistor to delay the discharge time when the closed electric circuit is formed for signaling excessive intraocular pressure above a predetermined threshold pressure, to avoid/reduce artifacts such as momentary pressure spiking due to eye rubbing. One further aspect of the invention provides an optical readout from the timer, wherein an external instrument is capable of optically activating the optical readout, receiving the optical readout, and/or monitoring ambient atmospheric pressure. In another aspect of the invention the external instrument is capable of optically powering the pressure sensor device.

It is still another object of the present invention to provide a method for signaling excessive intraocular pressure of an eye above a predetermined threshold pressure, comprising: providing a sensor device sized and configured to be placed in the anterior chamber of an eye, wherein the device comprises a pressure switch activatable when the intraocular pressure of an eye is higher than the predetermined threshold pressure; recording time, date, and duration with a timer that is associated with the pressure switch when the pressure switch is activated, wherein the time, date, and duration is converted to optically readable data through an optical readout system; activating an external instrument to read the data, wherein the instrument is capable of wirelessly optically activating the optical readout system. One further aspect of the invention provides a means for the external instrument to allow the intraocular pressure data as well as the time, date, and duration data to be downloaded to a computer and/or PDA and to be transmitted over the Internet to a central location such as a physician's office.

BRIEF DESCRIPTION OF THE DRAWINGS

Further features and advantages of the present invention will become apparent to one of skill in the art in view of the Detailed Description of Exemplary Embodiments that follows, when considered together with the attached drawings and claims.

DETAILED DESCRIPTION OF EXEMPLARY EMBODIMENTS

The preferred embodiments of the present invention described below relate particularly to an optically powered and optically data-transmitting wireless intraocular pressure sensor that can be implanted in the anterior chamber of an eye by securing it onto the peripheral iris tissue or onto an intraocular lens out of line-of-sight. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

Figure 1:
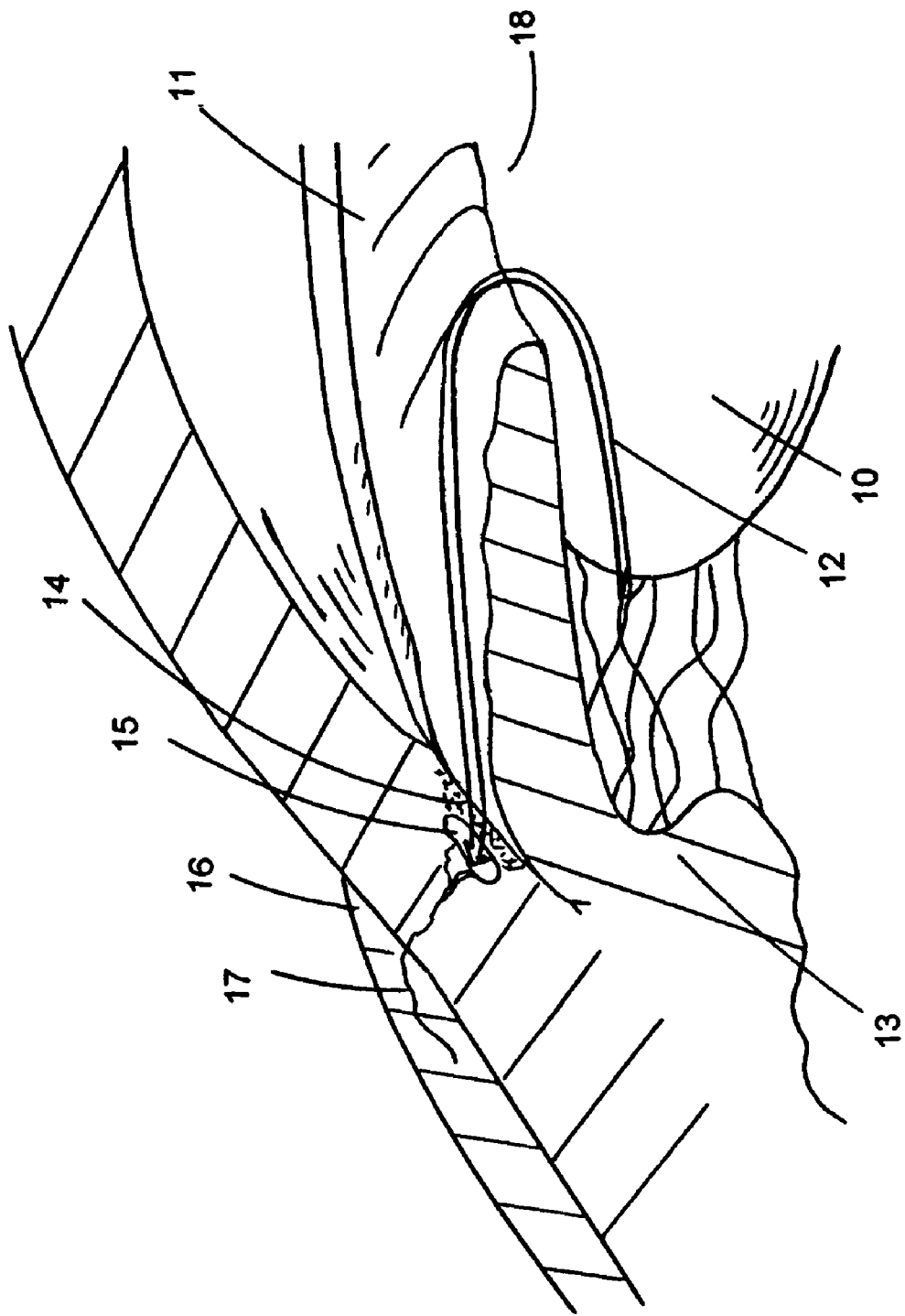
FIG. 1 illustrates a general aqueous flow around the front section of an eye.

FIG. 1 illustrates a general aqueous flow 12 around the front section of an eye, showing relative anatomical locations of the trabecular meshwork 14, the anterior chamber 18, and Schlemm's canal 15. The cornea 19 (FIG. 6) is a thin transparent tissue that focuses and transmits light into the eye and through a pupil 8 and the lens 10. The pupil is a circular hole in the center of an iris 11 (colored portion of the eye). The cornea 19 merges into the sclera 7 at a juncture referred to as a limbus 16. A ciliary body 13 extends along the interior of the sclera 7. The anterior chamber 18 of the eye, which is bound anteriorly by the cornea 19 and posteriorly by the iris 11 and a lens 10, is filled with aqueous humor (hereinafter referred to as "aqueous"). Aqueous is produced primarily by the ciliary body 13, then moves anteriorly through the pupil 8 and reaches an anterior chamber angle, formed between the iris 11 and the cornea 19. In a normal eye, aqueous is removed from the anterior chamber 18 through the trabecular meshwork 14. Aqueous passes through the trabecular meshwork 14 into Schlemm's canal 15 and thereafter through a plurality of aqueous veins 17, which merge with blood-carrying veins, and into systemic venous circulation. Intraocular pressure is maintained by an intricate balance between secretion and outflow of aqueous in the manner described above. Glaucoma is, in most cases, characterized by an excessive buildup of aqueous in the anterior chamber 18 which leads to an increase in intraocular pressure. Fluids are relatively incompressible, and thus intraocular pressure is distributed relatively uniformly throughout the eye.

Figure 2:
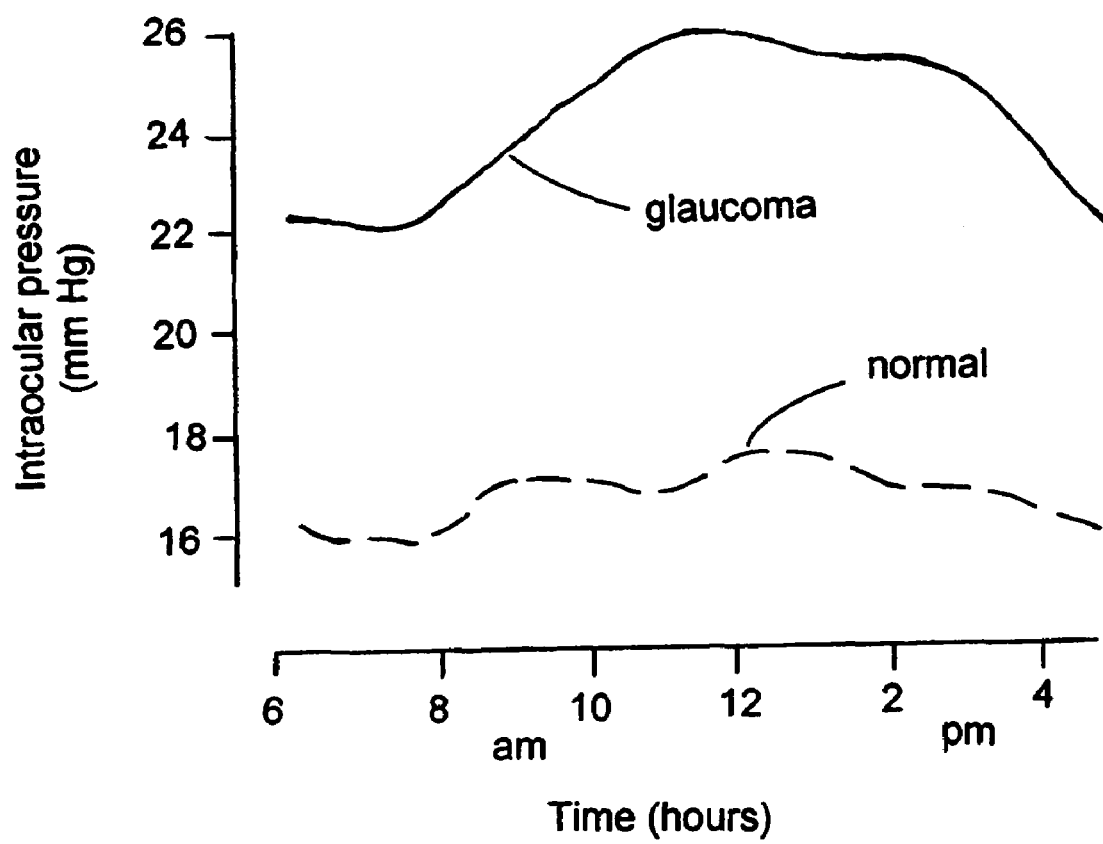
FIG. 2 shows IOP changes during the day for an average normal eye and a glaucoma eye.

FIG. 2 shows diurnal variation in IOP in both normal (the lower curve) and glaucomatous (the upper curve) eyes. It is known that the IOP within the same eye of a person undergoes drastic changes (oscillations) during the 24 hours in a day. Thus a pressure measurement at a doctor's office can at best only get a snapshot in time of the currently prevailing intraocular pressure, missing all the other pressure oscillations. Consequently a sporadic IOP measurement may still not prevent glaucomatous damage from happening. The normal IOP is typically less than 20 mmHg, though some variation exists. It is one object of the present invention to provide a wireless intraocular pressure sensor that enables detecting an IOP violating a predetermined pressure threshold on a 7-day 24-hour cycle.

A self-checking non-contact IOP monitoring system with frequent readout that measures the true intraocular pressure is very important and much needed. Beyond the screening for high IOP there are issues related to drug therapy for glaucoma and how to titrate and monitor these treatments. While on therapeutic eye drops one often sees salient and transient periods of breakthrough elevation of the IOP which can damage the eye. Therefore, we would like our proposed wireless intraocular pressure sensor (WIPS) to red flag even one such violation of a predetermined threshold pressure or pressures. This close monitoring of the IOP would greatly help the control and optimization of glaucoma drug therapy, especially for patients that already have the diagnosis of glaucoma.

Figure 3:
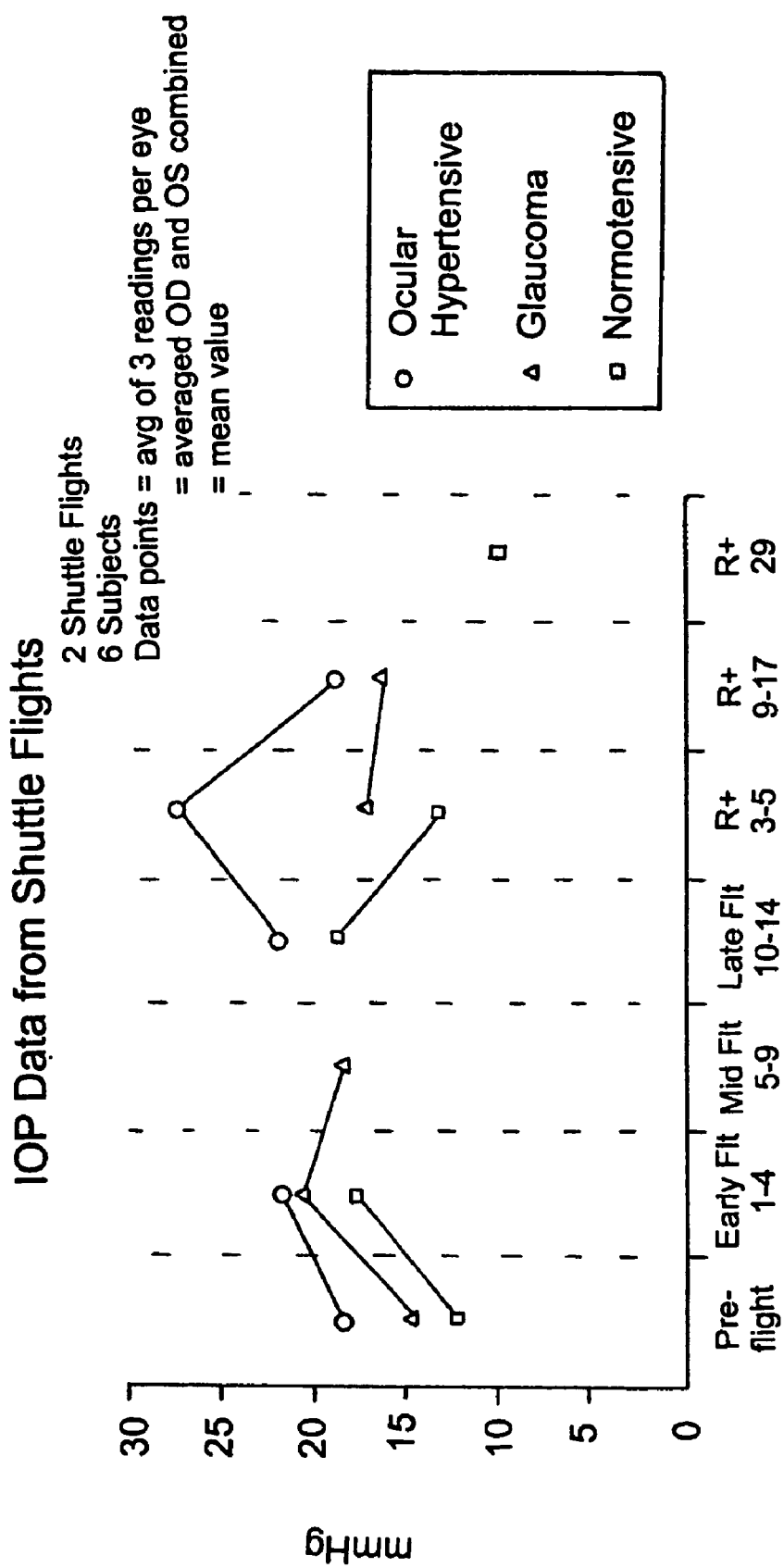
FIG. 3 shows IOP data from NASA Johnson Space Center (JSC) shuttle flight.

According to the Space Medicine Office at NASA's Johnson Space Center, intraocular hypertension and intracranial hypertension due to microgravity are known problems in the operative environment of space flight. FIG. 3 shows shuttle flight IOP data from NASA Johnson Space Center. From a JSC-NASA point of view, it is essential to monitor IOP during long space missions for timely management before astronaut performance is impaired or permanent damage incurred. The medical conditions of astronauts are usually not available to people on Earth unless a remote sensor is in place. One aspect of the invention is to provide a WIPS that is accurate and small enough to be implantable in the eye to continuously or on demand monitor the intraocular pressure. Another aspect of the invention relates to a method for self-checking intraocular pressure of a patient comprising: providing an optically powered and optically data-transmitting wireless intraocular pressure sensor device for detecting excessive intraocular pressure above a predetermined threshold pressure, wherein the device comprises an external instrument comprising means for receiving optical readout of detected excessive intraocular pressure; and self-checking the detected excessive intraocular pressure by activating the external instrument by the patient. Further, the sensor device comprises a pressure switch that is sized and configured to be placed in the anterior chamber of an eye of the patient, wherein the pressure switch is activated when the intraocular pressure is higher than the predetermined threshold pressure.

In one aspect, the WIPS may comprise an extremely small nano-technology based piezoresistive or capacitive sensor that is coated with a biocompatible polymer film, for example, silicone film. In one embodiment, a pressure transducer comprises (a) a capacitive pressure sensor, the pressure sensor including a diaphragm, at least part of the diaphragm moving in response to changes in a pressure; and (b) an electronic circuit, the circuit generating an output signal representative of the pressure. Some aspect of the invention provides an external LED instrument capable of optically activating the IR photodiode, which has an extremely low dark current and is shielded against ambient light, e.g., by means of a narrow IR filter, and triggering the indicator LED optical readout.

Figure 4:
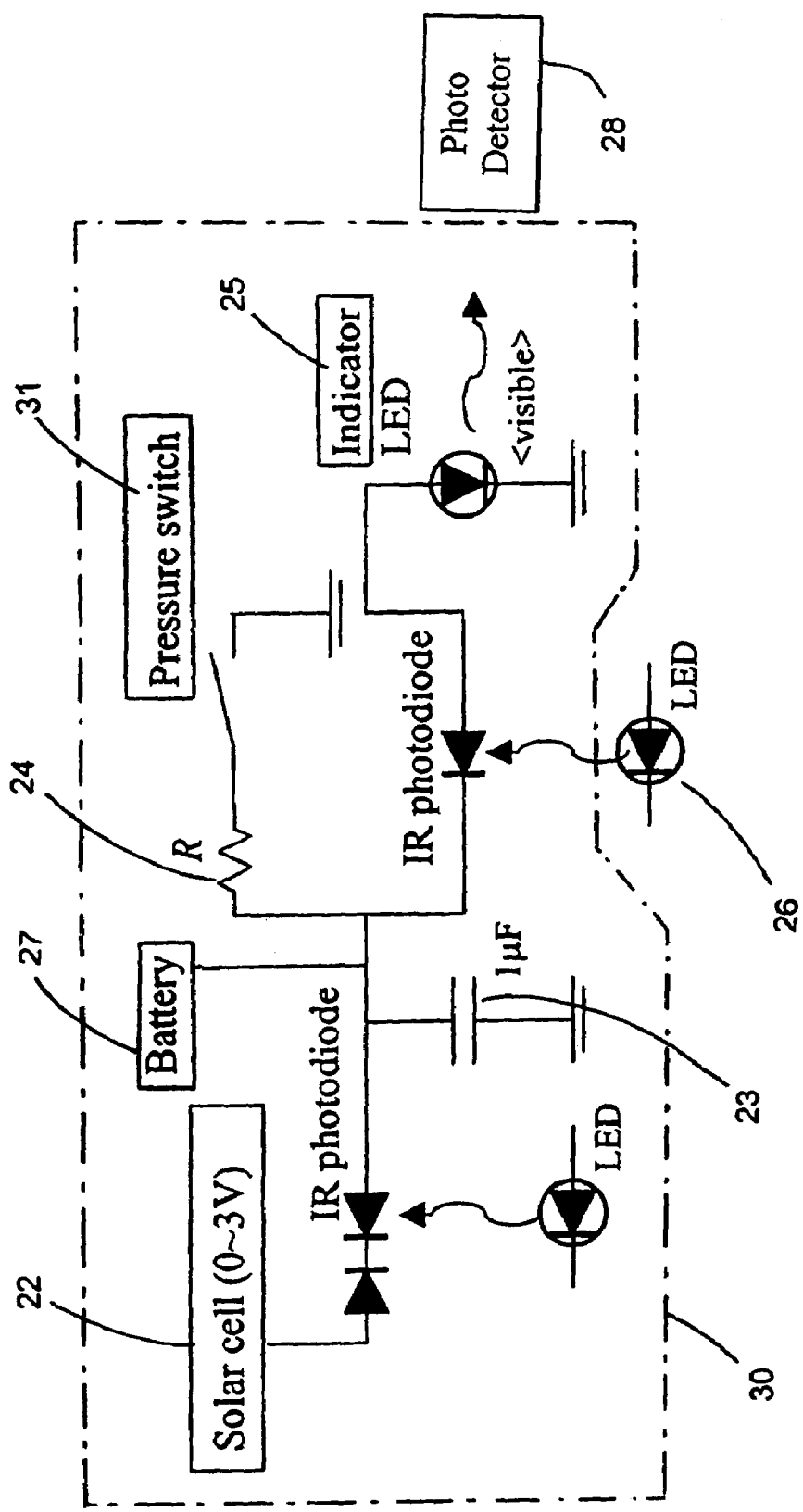
FIG. 4 is a schematic drawing of the IOP sensor device according to the principles of the present invention.

FIG. 4 shows one embodiment of the intraocular pressure sensing system. The pressure sensor device 30 is implantable in an eye and comprises a pressure switch 31 with a circuit, a solar cell system 22 or a battery power supply 27. The solar cell is charged during daytime and when eyes are open. Electricity is converted from solar power via microphotodiodes solar cells mechanism when light enters through clear and translucent tissues of the eye. The power density of a typical solar cell is about 0.15 mW/mm$^2$ in normal irradiation. Given an extraterrestrial solar input of 1.367 mW/mm$^2$ (solar constant), roughly 10 times the necessary power density is provided which is reduced down to 30% on a very cloudy day due to atmospheric absorption (Solar Energy 1976;18(4):309). The cornea of an eye has a high transmittance in the visible spectrum with the exception of UV, thus there will be no significant additional loss of light penetrating the eye and powering the solar cell attached to the iris in the anterior chamber. A solar cell as a power source for a WIPS would provide adequate energy for continuously or on demand monitoring the intraocular pressure. Once the pressure switch 31 is triggered (that is, the pressure exceeds a preset critical IOP threshold value), the capacitor 23 is fully discharged through the indicator LED 25. In some embodiment, the pressure switch is resettable.

In some aspect of the pressure sensor device 30, there is provided a resistor 24 in the electric circuit to eliminate any momentary pressure spiking due to rubbing an eye. By incorporating a resistor, the discharge time can be initially set (the discharge time is determined by the resistor constant) to about 1 minute or longer, so that the capacitor is not fully discharged during the time for rubbing an eye.

In one embodiment, the solar cell is sized and configured with about 2–4 mm$^2$ light receiving area enabling power supply of about 300–600 µW. The pressure switch system 31 is configured being sufficiently powered by the solar cell even in dim light conditions. The solar cell also contains a capacitor 23 that will be charged during daylight with the eye open. In one embodiment, this capacitor is the power source for the intraocular pressure sensing circuit during closed-eye conditions, including night time.

A wavelength specific and intensity dependent photoreceptor, e.g., IR photodiode, which has an extremely low dark current and is shielded against ambient light, e.g., by means of a narrow IR filter, is activated only by a solid state laser diode of the same wavelength and sufficient intensity. It is to check whether the capacitor remains charged or not. When the switch is activated (that is, shorted), the charge in the capacitor emits light through the indicator LED 25, detected by an external photo detector, if the IOP did not exceed the preset critical value since the last readout. In other words, it is some aspect of the invention to provide an external LED instrument 26 capable of wirelessly optically activating the IR photodiode and triggering the indicator LED optical readout 25 to be received by an external photo detector 28. In another embodiment instead of using dynamic RAM such as provided by capacitors, static RAM (SRAM) is used to power the pressure switch and the optical LED readout.

Upon querying the wireless optical readout module two possible scenarios can occur. First scenario with capacitor or SRAM discharged: Using an external solid state laser diode will not cause the LED to light up since the capacitor is already discharged, thus denoting that the critical or threshold IOP value has been exceeded since the last time the capacitor was discharged. Second scenario with capacitor or SRAM charged: Using an external solid state laser diode will cause the LED to light up since the fully charged capacitor will be discharged, thus denoting that the critical or threshold IOP value has not been exceeded since the last time the capacitor was charged. In both scenarios the capacitor will be recharged instantly by the solar cell through the IR diode after the query event. The switch is also a wavelength specific and intensity dependent photoreceptor, which has an extremely low dark current and is shielded against ambient light, e.g., by means of a narrow IR filter, that is only activated by a second solid state laser diode of different wavelength than the one used for activating the other switch and sufficient intensity. In one aspect of the invention, a timer or recorder is provided to bring out the "memory" effect to reveal a threshold (or a plurality of thresholds) violation in the past.

Figure 5A:
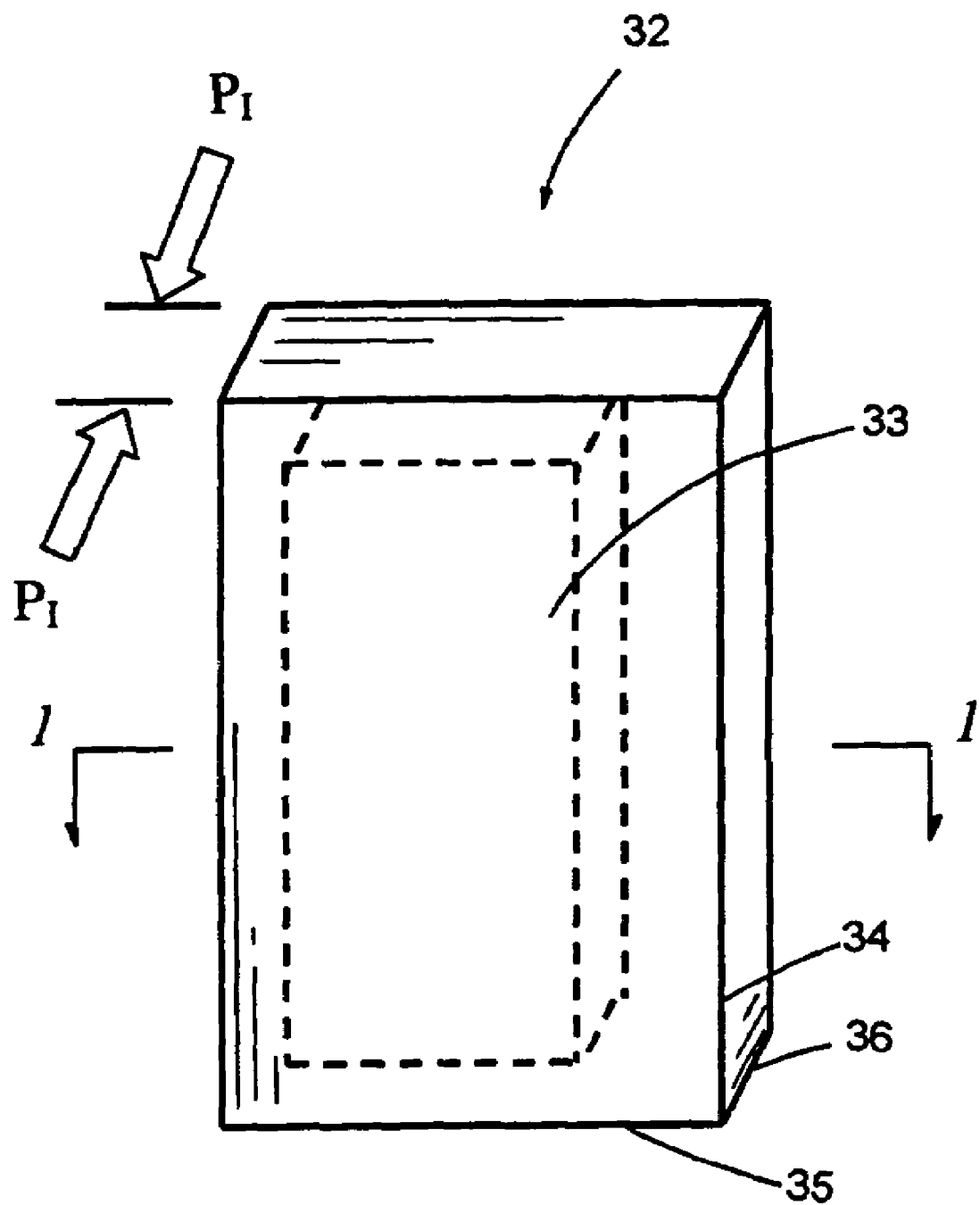
FIG. 5A is an embodiment of the pressure switch enclosure according to the principles of the invention.

FIG. 5A shows one embodiment of the pressure switch enclosure 32, which comprises a compressible (for example, gas-filled) or vacuum interior space 33 surrounded by a membrane construct having a height 34, a width 35 and a depth 36. The membrane construct is sized and configured enabling the intraocular pressure $P_I$ to cause significant dimensional changes to the depth 36, and insignificant dimensional changes to the height 34 and the width 35. By way of example, the membrane material in the depth dimension is substantially more compressible than the membrane material in the height or width dimension.

Figure 5B:
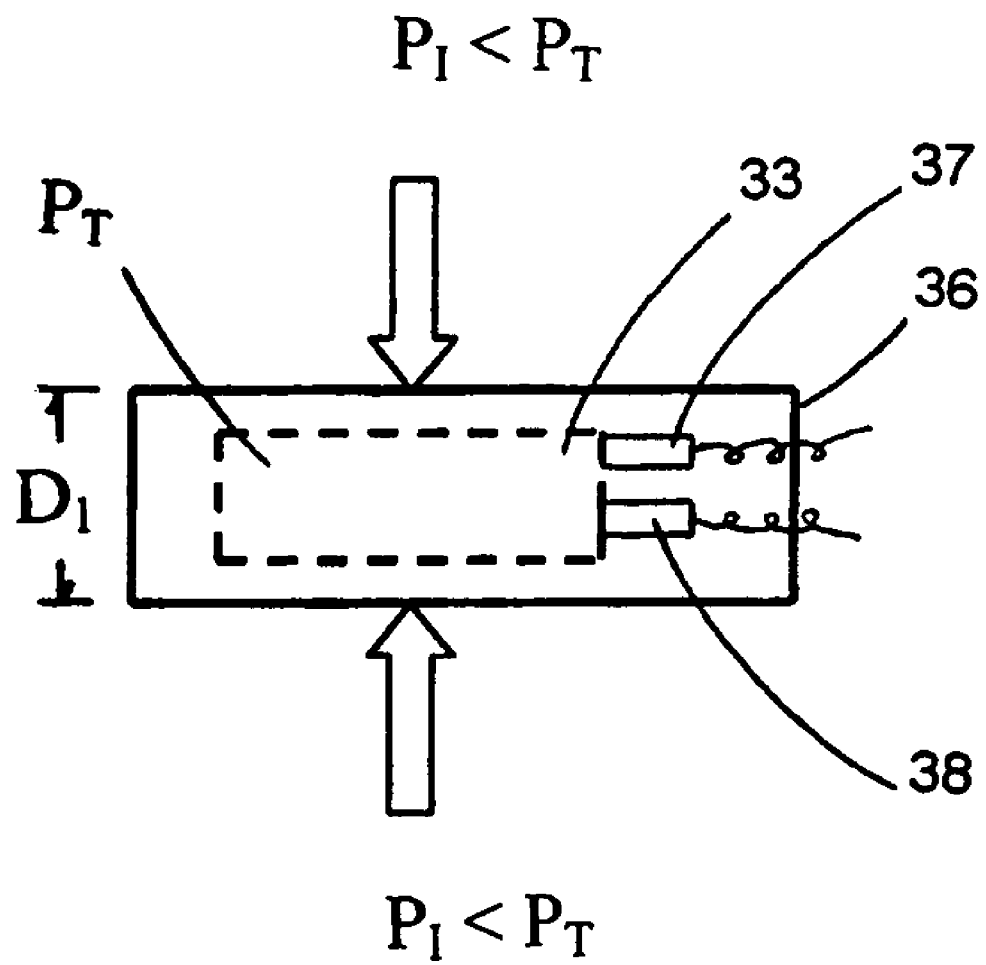
FIG. 5B is a cross-sectional view of section 1—1 of FIG. 5A, illustrating the pressure switch principles when the IOP is less than the predetermined threshold pressure.

FIG. 5B shows a cross-sectional view of section 1—1 of FIG. 5A, illustrating the pressure switch principles when the intraocular pressure $P_I$ is less than the threshold pressure $P_T$. Under such a condition, the length of the depth 36 is $D_1$. The enclosure 32 further comprises a first electrode or electric contact 37 and a second electrode 38 that is spaced apart from the first electrode 37 when the length of the depth is about $D_1$.

Figure 5C:
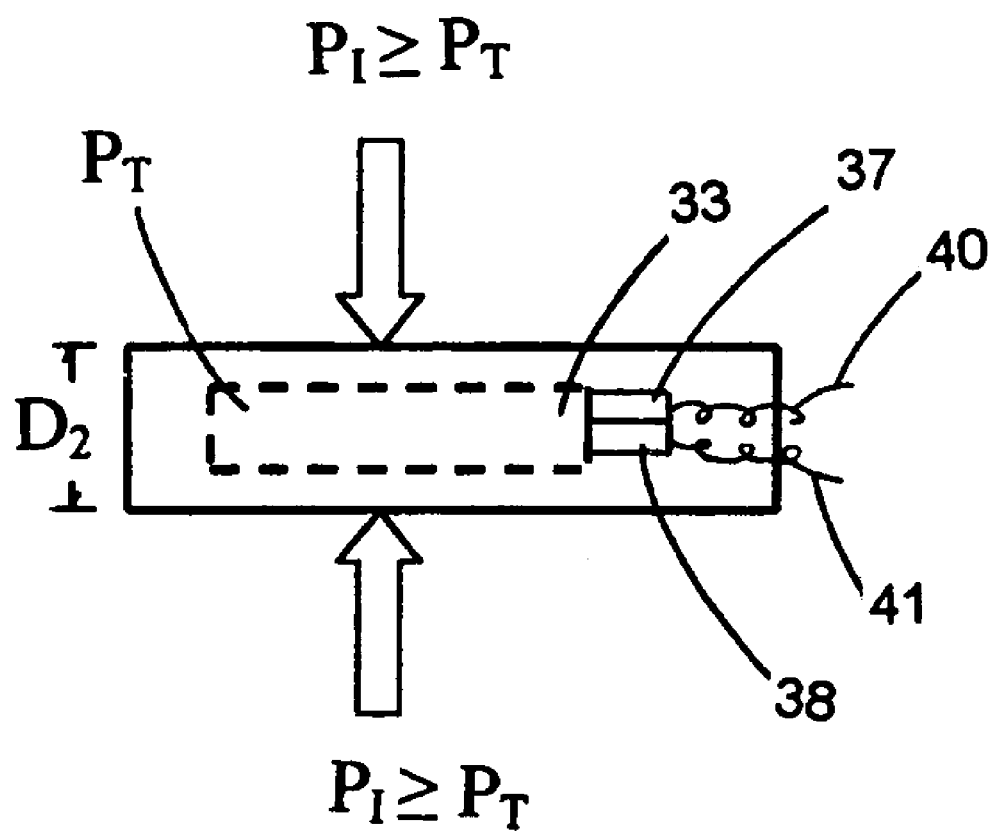
FIG. 5C is a cross-sectional view of section 1—1 of FIG. 5A, illustrating the pressure switch principles when the IOP is equal to or greater than the predetermined threshold pressure.

FIG. 5C shows a cross-sectional view of section 1—1 of FIG. 5A, illustrating the pressure switch principles when the intraocular pressure $P_I$ is equal to or greater than the threshold pressure $P_T$. Under this condition, the length of the depth 36 has been compressed from $D_1$ to $D_2$ and thereafter, the two electrodes 37, 38 contact with each other to form a closed electric circuit with conductors 40, 41, respectively connecting to the capacitor 23. Thus, the pressure surge activates the signal recording and/or timing recording.

Some aspects of the invention relate to a pressure sensor device for signaling excessive intraocular pressure above a threshold pressure, comprising a pressure switch 31 that is sized and configured to be placed in the anterior chamber 18 of an eye, wherein the pressure switch is activated when the intraocular pressure is higher than the threshold pressure, wherein the pressure switch is a micro electromechanical system.

One aspect of the invention relates to the pressure switch comprising a first electrode and a second electrode mounted onto a compressible enclosure, the electrodes being sized, configured and positioned spaced apart when the intraocular pressure is lower than the predetermined threshold pressure, and wherein the first electrode contacts the second electrode to make a closed electric circuit when the intraocular pressure becomes higher than the threshold pressure. In one embodiment, a timer is provided to record the time when the closed electric circuit is formed for signaling excessive intraocular pressure above a threshold pressure. In another embodiment, the pressure sensor device further comprises an optical readout 25 from the timer, wherein an external instrument 26 is capable of optically activating the optical readout. One aspect of the invention relates to the external instrument that optically powers at least one component of the device. In one embodiment, the external photo detector (that is, a reader) 28 may further comprise means for monitoring ambient atmospheric pressure. Means for monitoring ambient atmospheric pressure to be incorporated onto a photo detector is well known to one of skill in the art. The timer would record the onset of pressure violation and the duration, among other parameters, such as eye opening/closing. This data can be downloaded to a computer and/or PDA and transmitted over the Internet to a central location such as a physician's office.

Figure 6:
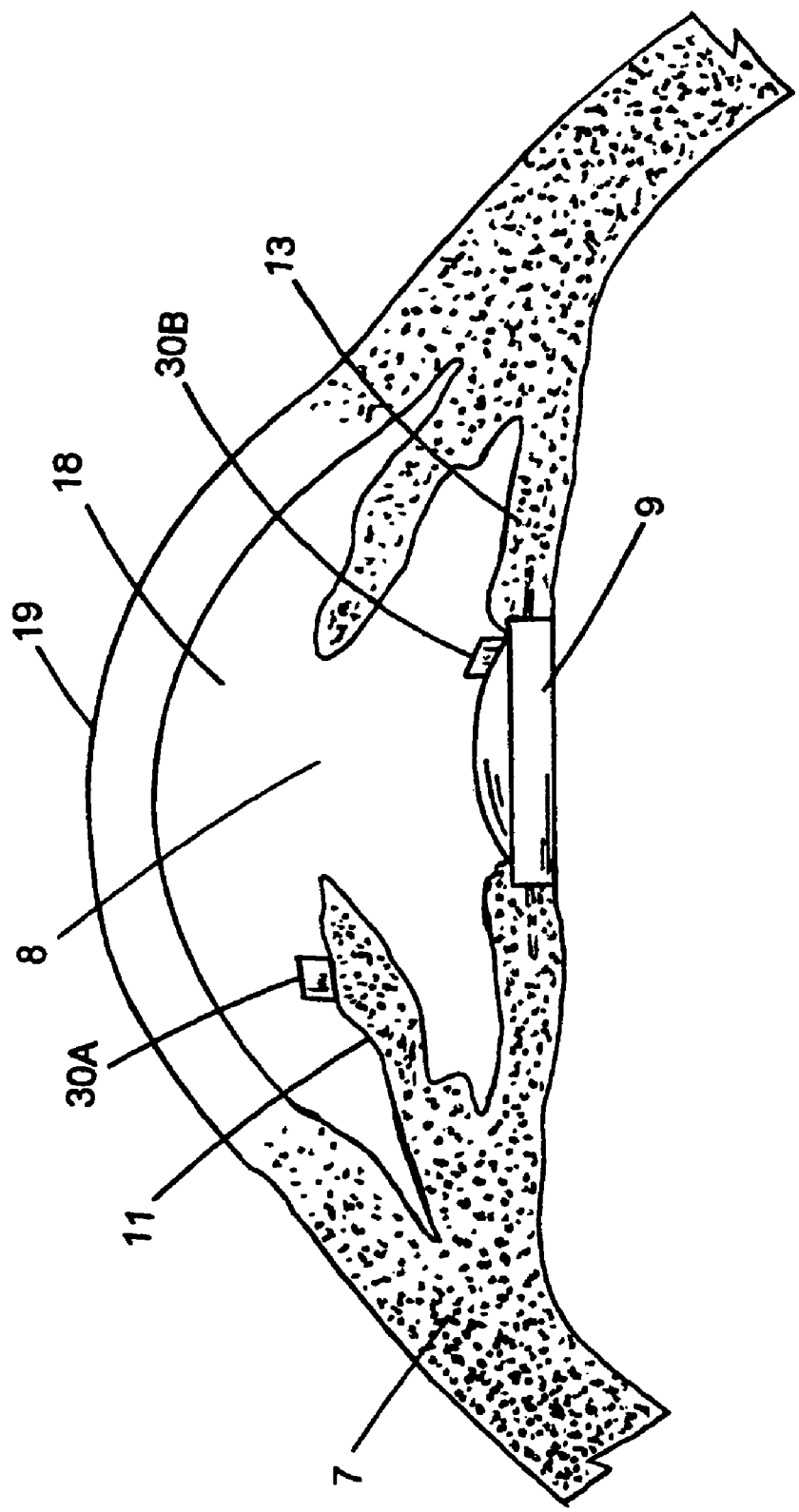
FIG. 6 shows one embodiment of the placement of a pressure sensor device inside an eye.

FIG. 6 shows the placement of a pressure sensor device inside an eye. In one embodiment, the pressure switch or the pressure sensor device 30A is placed on an iris 11 of the eye. In another embodiment, the pressure switch or the pressure sensor device 30B is placed on an intraocular lens 9 inside the eye. It is essential that the pressure sensor device is placed out of line-of-sight. Any conventional methods of attaching or securing the device on an iris, such as with an anchor, suture, hook or other fixation means are well known to one skilled in the art.

Some aspects of the invention relate to a pressure sensor device for signaling excessive intraocular pressure above a plurality of threshold pressures, comprising a plurality of pressure switches that are sized and configured to be placed in the anterior chamber of an eye, wherein a first pressure switch is activated when the intraocular pressure is higher than a first predetermined threshold pressure. The second pressure switch is activated when the intraocular pressure is higher than a second predetermined threshold pressure and so forth. By way of example, the first threshold pressure may be about 18 mmHg and the second threshold pressure is about 20 mmHg. Depending on an individual's health conditions, the threshold pressures may be slightly different from the typical values. In one embodiment, the first pressure switch comprises a pair of first electrodes mounted onto a first compressible enclosure, the pair of first electrodes being sized, configured and positioned spaced apart when the intraocular pressure is lower than the first predetermined threshold pressure, and wherein the pair of first electrodes contacts each other to make a closed electric circuit when the intraocular pressure becomes higher than the first predetermined threshold pressure. Some aspects of the invention provide a pressure sensor device that records and reveals the time, date, and duration when the measured intraocular pressure is higher than a predetermined threshold pressure on a continuous or semi-continuous or on-demand basis.

Further aspects of the invention relate to a method for signaling excessive intraocular pressure of an eye above a predetermined threshold pressure, comprising: (a) providing a sensor device sized and configured to be placed in the anterior chamber of an eye, wherein the device comprises a pressure switch activatable when an intraocular pressure of the eye is higher than the threshold pressure; (b) recording time, date, and duration with a timer that is associated with the pressure switch when the pressure switch is activated, wherein the time, date, and duration is converted to optically readable data through an optical readout system; and (c) activating an external instrument to read the data, wherein the instrument is capable of optically activating the optical readout system and/or comprises means for receiving the optical readout. A timer or time recorder to record the time when the pressure switch is activated is well known to one skilled in the art.

From the foregoing description, it will be appreciated that a novel intraocular pressure sensor for detecting excessive intraocular pressure above a predetermined threshold pressure and methods of use have been disclosed. While aspects of the invention have been described with reference to specific embodiments, the description is illustrative and is not intended to limit the scope of the invention. Various modifications and applications of the invention may occur to those who are skilled in the art, without departing from the true spirit or scope of the invention. The breadth and scope of the invention should be defined only in accordance with the appended claims and their equivalents.

What is claimed is:

1. An wireless intraocular pressure sensor device for detecting excessive intraocular pressure above a predetermined threshold pressure, comprising:
   a pressure switch that is sized and configured to be placed in an eye, wherein said pressure switch is activated when the intraocular pressure is higher than the predetermined threshold pressure; and
   an optical output configured to be placed in the eye and electrically connected to the pressure switch, wherein the state of the optical output indicates whether the pressure switch was activated.

2. The device of claim 1, wherein the pressure switch is a micro electromechanical system.

3. The device of claim 1, wherein the pressure switch is placed on the iris of an eye.

4. The device of claim 1, wherein the pressure switch is placed on an intraocular lens.

5. The device of claim 1, wherein the pressure switch is placed on a glaucoma tube.

6. The device of claim 1, wherein the pressure switch is powered by a solar cell system.

7. The device of claim 1, wherein the pressure switch is powered by a battery.

8. The device of claim 1, wherein the pressure switch comprises a first electrode and a second electrode mounted onto a compressible enclosure, the electrodes being sized, configured and positioned spaced apart when the intraocular pressure is lower than the predetermined threshold pressure, and wherein the first electrode contacts the second electrode to make a closed electric circuit when the intraocular pressure becomes higher than the predetermined threshold pressure.

9. The device of claim 8, wherein a timer is provided to record the time, date, and duration when the closed electric circuit is formed for signaling excessive intraocular pressure above the predetermined threshold pressure.

10. The device of claim 9 further comprising an optical readout from the timer.

11. The device of claim 1, further comprising a resettable pressure switch.

12. The device of claim 1, further comprising an external instrument for optically activating the optical output.

13. The device of claim 12, wherein the external instrument comprises a sensor for receiving light from the optical output.

14. The device of claim 13, wherein the external instrument comprises means for monitoring ambient atmospheric pressure.

15. The device of claim 1, wherein the device is optically powered by an external instrument.

16. The device of claim 15, wherein the external instrument allows the intraocular pressure data as well as the time, date, and duration data to be at least one of downloaded to a computer, downloaded to a PDA, and to be transmitted over the Internet to a central location such as a physician's office.

17. An wireless intraocular pressure sensor device for detecting excessive intraocular pressure above a plurality of predetermined threshold pressures, comprising:
   a plurality of pressure switches that are sized and configured to be placed in an eye, wherein a first pressure switch is activated when the intraocular pressure is higher than a first predetermined threshold pressure; and
   an optical output configured to be placed in the eye and electrically connected to the plurality of pressure switches, wherein the state of the optical output indicates whether one or more of the pressure switches was activated.

18. The device of claim 17, wherein a second pressure switch is activated when the intraocular pressure is higher than a second predetermined threshold pressure.

19. The device of claim 17, wherein the pressure sensor device is a micro electromechanical system.

20. The device of claim 17, wherein the pressure sensor device is placed on the iris of an eye.

21. The device of claim 17, wherein the pressure sensor device is placed on an intraocular lens.

22. The device of claim 17, wherein the pressure sensor device is placed on a glaucoma tube.

23. The device of claim 17, wherein at least one of the plurality of pressure switches is powered by a solar cell system.

24. The device of claim 17, wherein at least one of the plurality of pressure switches is powered by a battery.

25. The device of claim 18, wherein the second predetermined threshold pressure is higher than the first predetermined threshold pressure.

26. The device of claim 17, wherein the first pressure switch comprises a pair of first electrodes mounted onto a first compressible enclosure, the pair of first electrodes being sized, configured and positioned spaced apart when the intraocular pressure is lower than the first predetermined threshold pressure, and wherein the pair of first electrodes contacts each other to make a closed electric circuit when the intraocular pressure becomes higher than the first predetermined threshold pressure.

27. The device of claim 26, wherein a timer is provided to record the time, date, and duration when the closed electric circuit is formed for a signaling excessive intraocular pressure above the predetermined threshold pressure.

28. The device of claim 27 further comprising an optical readout system from the timer.

29. The device of claim 17, further comprising resettable pressure switches.

30. The device of claim 17, further comprising an external instrument for optically activating the optical output.

31. The device of claim 30, wherein the external instrument comprises a sensor for receiving light from the optical output.

32. The device of claim 30, wherein the external instrument comprises means for monitoring ambient atmospheric pressure.

33. The device of claim 17, wherein the device is optically powered by an external instrument.

34. The device of claim 33, wherein the external instrument allows the intraocular pressure data as well as the time, date, and duration data to be at least one of downloaded to a computer, downloaded to a PDA, and to be transmitted over the Internet to a central location such as a physician's office.

35. A method for self-checking intraocular pressure of a patient comprising:

implanting an optically data-transmitting wireless intraocular pressure sensor device for detecting excessive intraocular pressure above a predetermined threshold pressure into an eye of a patient;

checking the pressure sensor device with an external instrument comprising a sensor for wirelessly receiving an optical signal from an optical output implanted in the eye and electrically connected to the pressure sensor device indicative of detected excessive intraocular pressure.

36. The method of claim 35, wherein said sensor device comprises a pressure switch that is sized and configured to be placed in the anterior chamber of an eye of the patient, wherein said pressure switch is activated when the intraocular pressure is higher than the predetermined threshold pressure.

37. The method of claim 35, wherein implanting comprises places the pressure sensor device on one of an intraocular lens, a glaucoma tube, and an iris.

38. The device of claim 13, wherein receiving light from the optical output comprises receiving light emitted from the optical output.

39. The device of claim 31, wherein receiving light from the optical output comprises receiving light emitted from the optical output.

40. The device of claim 17, wherein the optical output comprises at least one optical output for each of the plurality of pressure switches.

* * * * *

UNITED STATES PATENT AND TRADEMARK OFFICE
CERTIFICATE OF CORRECTION

| | |
|---|---|
| PATENT NO. | : 7,131,945 B2 |
| APPLICATION NO. | : 10/686492 |
| DATED | : November 7, 2006 |
| INVENTOR(S) | : Fink et al. |

Page 1 of 1

It is certified that error appears in the above-identified patent and that said Letters Patent is hereby corrected as shown below:

Please insert the following new paragraph as the second paragraph on page 1, line 15:

GOVERNMENT CONTRACT

The invention described herein was made in the performance of work under NASA Contract No. 30861, and is subject to the provisions of Public Law 96-517 (35 U.S.C. 202) in which the Contractor has elected to retain title.

Signed and Sealed this

Sixth Day of March, 2007

JON W. DUDAS
*Director of the United States Patent and Trademark Office*

UNITED STATES PATENT AND TRADEMARK OFFICE
CERTIFICATE OF CORRECTION

PATENT NO. : 7,131,945 B2 Page 1 of 1
APPLICATION NO. : 10/686492
DATED : November 7, 2006
INVENTOR(S) : Fink et al.

It is certified that error appears in the above-identified patent and that said Letters Patent is hereby corrected as shown below:

Title Page, Item (75) Inventors, delete "Yu-Chong Tai" and "Ellis Meng"

In Claim 1, column 9, line 57, please correct "An wireless intraocular" to read -- A wireless intraocular --

In Claim 17, column 10, line 46, please correct "An wireless intraocular" to read -- A wireless intraocular --

In Claim 37, column 12, line 26, please correct "places the pressure" to correctly read -- placing the pressure --

Signed and Sealed this

Nineteenth Day of June, 2007

JON W. DUDAS
*Director of the United States Patent and Trademark Office*